United States Patent [19]

Shah

[11] 4,300,820
[45] Nov. 17, 1981

[54] WATER ABSORPTIVE COMPOSITION

[75] Inventor: Kishore R. Shah, Chelmsford, Mass.

[73] Assignee: The Kendall Company, Walpole, Mass.

[21] Appl. No.: 201,349

[22] Filed: Oct. 27, 1980

Related U.S. Application Data

[63] Continuation-in-part of Ser. No. 100,375, Dec. 5, 1979, abandoned, which is a continuation-in-part of Ser. No. 957,885, Nov. 6, 1978, abandoned.

[51] Int. Cl.³ .................. C08L 39/04; C08L 45/00; G02C 7/04
[52] U.S. Cl. .................. 351/160 H; 260/29.6 WB; 424/80; 525/205; 525/206
[58] Field of Search .................. 525/205, 206; 260/29.6 WB; 351/160 H; 424/80

[56] References Cited

U.S. PATENT DOCUMENTS

| | | | |
|---|---|---|---|
| 2,658,045 | 11/1953 | Schnildknecht | 260/29.6 HN |
| 2,901,457 | 8/1959 | Stoner | 525/205 |
| 3,159,539 | 12/1964 | Mendelsohn et al. | 424/80 |
| 3,511,659 | 7/1970 | Dennis, Jr. et al. | 525/205 |
| 3,700,761 | 10/1972 | O'Driscoll | 264/1 |
| 3,728,317 | 4/1973 | Blank | 264/1 |
| 3,803,093 | 4/1974 | Neefe | 526/303 |
| 3,807,398 | 4/1974 | Grucza | 264/1 |
| 3,933,766 | 1/1976 | Hofmann et al. | 351/160 H |
| 3,937,680 | 2/1976 | de Carle | 351/160 H |
| 3,949,021 | 4/1976 | Kunitomo et al. | 525/205 |
| 3,975,570 | 12/1975 | Ono | 525/205 |
| 4,018,853 | 4/1977 | Le Boeuf et al. | 525/283 |
| 4,067,839 | 1/1978 | Schultz | 264/1 |

OTHER PUBLICATIONS

Boyer-Kawenoki, Comptes Rendus, Ser C, vol. 263, pp. 278-281 (1966).
Chem. Abs., vol. 65, 20283d (1966).

Primary Examiner—J. Ziegler

[57] ABSTRACT

A composition capable of absorbing more than 45% of its weight of water without dissolution at room temperature to form a hydrogel is made by blending (1) 40 to 98% by weight of water-soluble polymer of a vinyl lactam having the structure

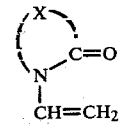

in which X represents an alkylene bridge having three to five carbon atoms or a copolymer thereof with 1 to 90 mole percent of a copolymerizable monomer containing a polymerizable ethylenic unsaturation; and (2) 2 to 60% by weight of a water-insoluble copolymer formed of 50% to 90% by weight based on the total copolymer of a hydrophobic water-insoluble ethylenically unsaturated monomer, 2 to 12% by weight of an ethylenically unsaturated monomer containing an acid group, and 0 to 50% by weight of a hydrophilic ethylenically unsaturated monomer free from acidic groups.

11 Claims, No Drawings

WATER ABSORPTIVE COMPOSITION

This application is a continuation-in-part of applicant's copending application Ser. No. 100,375 filed Dec. 5, 1979 abandoned, which is in turn a continuation-in-part of application Ser. No. 957,885 filed Nov. 6, 1979 abandoned.

This invention relates to a composition capable of absorbing more than 45% of its weight of water without dissolution at room temperature to form a hydrogel and pertains more specifically to an optically clear blend of a water-soluble poly(vinyl lactam) or of a water-soluble copolymer of a vinyl lactam with 1 to 90 mole percent of copolymerizable monomer containing a polymerizable ethylenic unsaturation, with a water-insoluble copolymer consisting essentially of 50% to 90% by weight based on the total weight of the copolymer of a hydrophobic water-insoluble ethylenically unsaturated monomer, 2% to 12% by weight of an ethylenically unsaturated monomer containing an acid group, and 0 to 50% by weight of a hydrophilic ethylenically unsaturated monomer free from acidic groups. Preferably the vinyl lactam is N-vinyl-2-pyrrolidone.

It has previously been proposed to insolubilize polymeric N-vinyl lactams such as poly(vinyl pyrrolidone) by reaction with water-soluble polymers containing carboxyl groups, the reaction product precipitating from solution when the two are mixed, as described in Stoner U.S. Pat. No. 2,901,457. As pointed out by Stoner et al. at column 4, lines 56-73, the reaction product there described always has substantially the same properties and contains the two polymeric components in the same proportions regardless of the proportions of the two used to make the product. The compositions of the present invention, on the other hand, vary in properties and in proportions of components depending upon proportions of starting materials. It has also been proposed in O'Driscoll et al. U.S. Pat. No. 3,700,761, in Grucza U.S. Pat. No. 3,807,398, and in Le Boeuf et al. U.S. Pat. No. 4,018,853 to make covalently cross-linked hydrogels by polymerizing hydrophilic methacrylate monomers in the presence of poly(vinyl pyrrolidone). Moreover, it has been reported in Boyer-Kawenoki, Compt. Rend., Ser. C, Vol. 263, p. 278 (Chem. Abs. Vol. 65, 20283d) 1966 that an I.R. spectrum of the addition product of poly(vinyl pyrrolidone) and poly(acrylic acid) indicated hydrogen bonding between the pyrrolidone carbonyl groups and the carboxyl groups of the poly(acrylic acid). In Ono et al. U.S. Pat. No. 3,975,570, it has been proposed to improve the moisture permeability of conventional pressure-sensitive adhesives which are copolymers of alkyl acrylates with acrylic or methacrylic acid by blending with them hydroxyethyl cellulose, and it was stated that blends of such adhesives with poly(vinyl pyrrolidone) did not exhibit improved moisture permeability. Other blends of a poly(vinyl lactam) with various copolymers are described and claimed in copending applications of Shah Ser. No. 137,297 filed Apr. 4, 1980 and of Shah and Temin Ser. No. 142,986 filed Apr. 23, 1980.

The compositions of the present invention are capable of absorbing more than 45% of their own weight of water when immersed in water at room temperature and may absorb even more than ten times their weight of water. Despite the absorption of such large amounts of water, the compositions retain their coherence and dimensional integrity and do not dissolve; these characteristics make them particularly useful for several biomedical purposes which require that the hydrogel come into intimate contact with body tissues or cavities.

The mechanism of interaction between the water-soluble vinyl lactam (preferably vinyl pyrrolidone) polymer or copolymer and the water-insoluble copolymer in the blend is not fully understood, but the blend does behave like a physical mixture rather than a chemical reaction product in that it can be separated into the two polymeric components by gel permeation chromatography. The blends are optically clear and substantially free from haziness, indicating that the blend is homogeneous despite the fact that the vinyl lactam polymer or copolymer is water-soluble and the copolymer is water-insoluble. Examination at high magnification under an electron microscope shows the presence of microphase domains (4000 Å or less in diameter) of water-insoluble material dispersed in the continuous phase of water-soluble vinyl lactam polymer or copolymer. The presence of these microphase domains of the water-insoluble copolymer prevents dissolution of the continuous phase polymer in water, but unlike covalent cross-linking of polymers does not render the blend non-thermoplastic. Instead, the blend possesses the ability to be repeatedly shaped or formed under moderate pressure at a temperature as low as 150° C., or in some cases even lower. The shaped or formed composition retains its shape at room temperature subject to distortion when swollen with water. The compositions of the present invention in which the dispersed submicroscopic particles (microphase domains) act as multiple cross-links to prevent dissolution of the hydrophilic continuous phase (which by itself is water-soluble), form a new class of hydrogels, distinct from those in which the cross-linking is provided by weak cohesive forces, hydrogen bonds, ionic bonds, or covalent bonds.

The N-vinyl lactams, polymers and copolymers of which can be used in the present invention include those having the structure

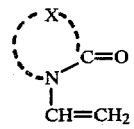

in which X represents an alkylene bridge having three to five carbon atoms, such as 1-vinyl-2-pyrrolidone, 1-vinyl-5-methyl-2-pyrrolidone, 1-vinyl-2-piperidone, and N-vinyl-ξ-caprolactam. The copolymerizable monomers with which the N-vinyl lactams can be copolymerized to form copolymers containing 10 to 99, preferably 25 to 99, mole percent N-vinyl lactam and correspondingly 1 to 90, preferably 1 to 75, mole percent of comonomer, include N,N-dimethyl acrylamide, glyceryl methacrylate, diethylene or triethylene glycol monomethacrylate or other hydrophilic monomers, as well as vinyl acetate, alkyl acrylate or methacrylate, vinyl alkyl ethers, acrylonitrile, vinyl chloride, or other hydrophobic monomers. In the case of monomers such as vinyl acetate which themselves form water-insoluble homopolymers, the upper limit of the amount of such monomer which can be employed to form the desired water-soluble copolymer is much lower than in the case of monomers such as N,N-dimethyl acrylamide which form water-soluble homopolymers. These polymers and copolymers may have molecular weights from 10,000 to 1,000,000 or more, but those having molecular weights from 100,000 to 1,000,000 are preferred. Polymers and copolymers of 1-vinyl-2-pyrrolidone are preferred.

The water-insoluble copolymers which can be employed as blends with the vinyl lactam polymer or copolymer in the compositions of the present invention include water-insoluble copolymers of a hydrophobic water-insoluble ethylenically unsaturated monomer such as alkyl esters of acrylic or methacrylic acid in which the alkyl group has from 1 to 16 carbon atoms, styrene, acrylonitrile, vinyl acetate, vinyl butyrate, vinyl chloride, vinylidene chloride, ethylene, propylene, butylene butadiene and other polymerizable alkadienes, vinyl alkyl ethers and vinyl alkyl ketones in which the alkyls have 3 or more carbon atoms, and the like. The copolymers also include as another essential monomer an ethylenically unsaturated monomer containing an acid group such as a carboxylic, sulfonic, or phosphonic acid group; among suitable acidic monomers are acrylic acid, methacrylic acid, crotonic acid, maleic acid, 2-sulfoethyl methacrylate, 1-phenyl vinyl phosphonic acid, and the like. The third monomer, is selected from a group of hydrophilic ethylenically unsaturated monomers, possessing a solubility parameter in excess of 11 [calories/cm$^3$]$^{\frac{1}{2}}$, free from acidic groups, such as methacrylamide, acrylamide, hydroxyethyl methacrylate, diethylene or triethylene glycol monomethacrylate, glyceryl methacrylate, etc.

In the case of each of the three types of monomers a mixture of two or more individual monomers of the same type can be used.

Compatibility or incompatibility of the water-insoluble copolymer with the water-soluble vinyl lactam polymer or copolymer in the hydrated form of the blend, that is, its suitability for use in the present invention, can in each case be readily determined by visual examination of a blend of the two polymers after equilibration in water at room temperature. If the blend is transparent and optically clear and remains so after immersion in water at 20° C. without dissolution in the water, it forms a satisfactory hydrogel. If the blend is cloudy or opaque after equilibration in water, or if it dissolves in water at 20° C., the blend made from that copolymer is not satisfactory and possesses poor mechanical properties. For a blend composition to possess satisfactory mechanical properties in the hydrated form, the size of the microphase domains of the terpolymer in the hydrogel should not be greater than 4,000 Å, and preferably should be below about 1000 Å.

The relative proportions of the different monomers in the water-insoluble copolymer may vary widely; the hydrophobic water-insoluble ethylenically unsaturated monomer may amount to 50% to 90% by weight, based on the total weight of copolymer, while the ethylenically unsaturated monomer containing an acidic group may amount to 2% to 12% by weight; the hydrophilic ethylenically unsaturated monomer may amount to 0 to 50% by weight. The exact proportions of the three types of monomers are determined by the hydrophobic-hydrophilic balance required in each case. In many cases, for attainment of this balance the incorporation of 15 to 45% of a hydrophilic monomer is required.

Thus, in the case of one preferred class of water-insoluble copolymers the amount of methyl methacrylate (or styrene or 2-ethylhexyl acrylate) is from 55 to 70% by weight based on the total copolymer weight, the amount of acrylic acid is from 2 to 12% by weight, and the amount of methacrylamide is from 25–43% by weight.

In the case of another preferred water-insoluble copolymer, the amount of n-butyl methacrylate is from 55 to 80% by weight based on the total copolymer weight, the amount of acrylic acid is from 2 to 12% by weight, and the amount of methacrylamide is from 15 to 35% by weight.

In the case of still another preferred water-insoluble copolymer, the amount of methyl methacrylate is from 88 to 90% by weight of the total copolymer, while 2-acrylamido-2-methyl propanesulfonic acid, the only other monomer constituent, is from 10–12% by weight. In this case, the presence of a non-acidic hydrophilic comonomer is not essential.

In the case of still another preferred water-insoluble copolymer, the amount of n-butyl methacrylate is from 50 to 78% by weight of the total copolymer, the amount of acrylic acid is from 2 to 12% by weight, and the amount of hydrophilic p-styrene sulfonamide is from 20 to 35% by weight. In another preferred water-insoluble copolymer, the amount of n-butyl methacrylate is from 55 to 70% of the total copolymer weight, acrylic acid is from 2 to 12%, and hydroxyethyl methacrylate is from 25 to 43%.

The relative proportions of water-soluble vinyl lactam polymer or copolymer and of water-insoluble copolymer in the blend vary over a wide range, from 40 to 98% by weight, preferably from 50 to 98%, based on the total weight of the blend, of the former and from 2 to 60% by weight, preferably from 2 to 50%, of the water-insoluble copolymer; optimum proportions of each within the range vary depending upon the particular properties desired in the blend as well as upon the identity of the particular polymer or copolymer present in the blend. The greater the proportion of the water-insoluble copolymer in the blend, the lower is the equilibrium water content of the resultant hydrogel. The water content of the blend hydrogels of this invention can be varied from approximately 30% to 95% or higher by judicious selection of the water-soluble and water-insoluble polymer and copolymer and its proportion in the blend, particularly when poly(N-vinyl-2-pyrrolidone) is the water-soluble component of the blend. In general, the higher the water content of the hydrogel, the poorer become its mechanical properties.

The blend can be made by mixing together solutions or dispersions of the water-soluble polymer or copolymer and of the water-insoluble copolymer in any desired vehicles or solvents which are miscible with each other, then removing the vehicle or solvent, as by evaporation. It may also be possible to blend the two components on a hot roll mill or in an extruder or in other conventional mixing equipment. Shaped articles of the blend can be prepared by casting from a suitable solvent or by a molding process under the influence of heat and pressure.

The thermoplasticity of these hydrogel-forming blends confers on them a special processing advantage over covalently cross-linked synthetic hydrogels. Tailoring of mechanical and physical properties (e.g., water content, solute and water permeability, softness, flexibility, tensile strength, etc.) of the hydrogel is readily accomplished by control of the physicochemical characteristics and the proportion in the blend of the water-insoluble copolymer. In addition, the physical properties of the blend can be modified by the inclusion of a compatible, water-soluble liquid plasticizer such as ethylene glycol, diethylene glycol, glycerine, or liquid polyethylene glycols (oxides) having molecular weights up to about 600 sold under the trade name Carbowax. Due to these advantages the novel hydrogel compositions of this invention lend themselves (when care is taken to exclude toxic plasticizers) to several applications such as burn and wound dressings, coatings for catheters and surgical sutures, soft contact lenses, implants for delivery of medicaments at controlled rates, and other articles coming into intimate contact with body tissues or cavities (e.g., vitreous and corneal prostheses).

These new hydrogel-forming materials can also be used in the manufacture of devices for controlled delivery of drugs which are sparingly soluble in water. When a drug (soluble in the water-insoluble copolymer) is incorporated in these hydrogels, it remains dispersed in hundreds of thousands of "depots" of water-insoluble domains. The delivery rate of the drug consequently is governed by partition coefficient of the drug in the aqueous and non-aqueous phases, membrane geometry, and the size and the number of the dispersed domains. An advantage of such a device is that a mechanical failure or a pin-hole would not cause any increase in the delivery rate of the drug.

A non-medical use of the novel compositions of this invention is for coating glass surfaces, such as inner sides of automotive and aircraft windshields, to render them non-fogging. This is accomplished by casting from a suitable solvent a thin coating of a blend composition, such as that described in Example 19, on a glass surface. Formation of the polymeric blend coating can also be accomplished by a spray of its dilute solution in a suitable solvent. The coating has a good adhesion to glass, is colorless, optically clear, and non-fogging upon exposure to hot, moist air.

The following specific examples are intended to illustrate more fully the nature of the present invention without acting as limitations upon its scope.

EXAMPLES 1-13

Each of the copolymers of these examples was prepared by conventional solution polymerization procedure by dissolving the desired proportions of monomers in a suitable solvent and by employing as an initiator of polymerization a small amount (0.2-0.4% by weight of monomers) of a free radical generator such as azobisisobutyronitrile or 2-t-butylazo-2-cyanopropane. Polymerization was carried out at 80°-95° C. to a high degree of conversion. The composition of the copolymerization mixtures is described in Table I. Copolymers of the Examples 1 to 4 were isolated from the reaction mixture by precipitation into methanol, collected by filtration, and dried at 100° C. under vacuum, whereas, the copolymer of Example 5 was isolated by removal of the volatiles by heating in vacuum at 100° C.

TABLE I

| REACTION INGREDIENTS | EXAMPLE NO. | | | | |
|---|---|---|---|---|---|
| | 1 | 2 | 3 | 4 | 5 |
| COMONOMERS - GRAMS | | | | | |
| Methyl Methacrylate | 65 | — | — | 90 | — |
| Methacrylamide | 30 | 30 | 15 | — | 30 |
| Styrene | — | 65 | — | — | — |
| Acrylic Acid | 5 | 5 | 5 | — | 5 |
| n-Butyl Methacrylate | — | — | 80 | — | — |
| 2-Acrylamido-2-methyl-propane Sulfonic Acid | — | — | — | 10 | — |
| 2-Ethylhexyl Acrylate | — | — | — | — | 65 |
| SOLVENT - MILLILITERS | | | | | |
| Ethanol | 100 | 100 | 100 | — | 100 |
| Dioxane | 100 | 100 | 100 | — | — |
| N,N-Dimethylformamide | — | — | — | 100 | 100 |

Each of the blend compositions of these examples was prepared by dissolving in N,N-dimethylformamide the desired proportions of the water-insoluble copolymer and poly(vinyl pyrrolidone) (Grade K-90, mol.wt. 360,000) to obtain a solution containing 10-15% by weight of the polymeric blend. The solution of the blend was then heated at 100° C. under vacuum to evaporate the solvent, leaving a mass of optically transparent blended solid material. The blend, which was thermoplastic, was pressed into a disc in a mold heated at 150° C. The molded disc was placed in deionized water for 72 hours, during which time it absorbed water and swelled to form a hydrogel. The compositions of the blends, their physical appearance, and the equilibrium water content of their hydrogels are described in Table II.

TABLE II

| | BLEND OF COMPOSITION | | | | |
|---|---|---|---|---|---|
| EXAMPLE NO. | COPOLYMER OF EXAMPLE NO. | PARTS BY WEIGHT OF PVP (K-90) PER 100 PARTS OF THE BLEND | PHYSICAL APPEARANCE | | EQUILIBRIUM WATER CONTENT WEIGHT % |
| | | | DRY FORM | HYDRATED FORM | |
| 6 | 1 | 70 | Transparent-Solid | Transparent, Strong | 68 |
| 7 | 1 | 90 | Transparent-Solid | Transparent, Strong | 91 |
| 8 | 2 | 70 | Transparent-Solid | Transparent, Strong | 58 |
| 9 | 2 | 90 | Transparent-Solid | Transparent, Strong | 80 |
| 10 | 3 | 90 | Transparent-Solid | Translucent, Coherent | 90 |
| 11 | 4 | 90 | Transparent-Solid | Transparent, Coherent | 84 |
| 12 | 5 | 70 | Transparent-Solid | Transparent, Strong | 77 |
| 13 | 5 | 90 | Transparent-Solid | Transparent, Strong | 90 |

EXAMPLES 14-15

A 20.8 g (0.10 mole) portion of phosphorus pentachloride was placed in a 500 ml. round-bottomed flask and 17.4 g (0.084 mole) of pulverized p-sodium styrenesulfonate was added slowly with ice bath cooling. The mixture was stirred cautiously with a magnetic stirrer. After 30 min. it was heated under reflux at 50°-60° C. for 2 hrs. The product was cooled and poured into 100 g of crushed ice and extracted with 100 ml of chloroform. The organic layer containing p-styrenesulfonyl chloride was separated, washed several times with distilled water, and dried over magnesium sulfate.

The chloroform solution (100 ml) containing p-styrenesulfonyl chloride was added with mechanical stirring into 340 ml of 30% ammonium hydroxide (specific gravity 0.90) while cooling with ice over a period of about 30 minutes. The mixture was heated to 50° C. for 5 hrs. under a reflux condenser and then cooled to room temperature.

The organic layer was separated, dried over anhydrous magnesium sulfate, and then evaporated to dryness to yield a solid white powder of crude p-styrenesulfonamide, which was purified by recrystallization from ethanol-water mixture to yield about 6.0 g of the sulfonamide, m.p. 130°-132° C.

The infrared spectrum of the sulfonamide showed absorptions at 3350 and 3260 cm$^{-1}$ (NH stretching), 1600 cm$^{-1}$ (aromatic c=c), 1305 and 1160 cm$^{-1}$ (S=O stretching), and 840 cm$^{-1}$ (p-disubstituted benzene, 2 adjacent CH wagging).

A copolymer of 62% n-butyl methacrylate, 30% p-styrenesulfonamide prepared as described above, and 8% acrylic acid was prepared in the usual way, as described in Examples 1-13, employing 33% concentration of the monomers in a mixture of ethyl alcohol and dioxane. The copolymer was purified by precipitation of the reaction mixture in chloroform, then isolated by filtration and dried in vacuo at 100° C.

Blends of the copolymer with poly(vinylpyrrolidone) (PVP, Grade K-90, mol.wt. 360,000) were prepared as described in Examples 1 to 13, by dissolving the copolymer and PVP in dimethylformamide and subsequently evaporating the solvent at 100° C. in vacuo. Blends containing 10% and 30% by weight of copolymer, respectively, the balance being poly(vinylpyrrolidone) in each case, were found to be optically transparent solids. Molded discs of the two blends, prepared as described in Examples 1 to 13, were found to absorb water and form transparent hydrogels containing 84.6% and 62.5% water by weight, respectively, when equilibrated with deionized water at room temperature for 72 hours.

EXAMPLES 16-19

Hydroxyethyl methacrylate (HEMA) was purified by extracting (4 to 6 times) a 1:1 solution of the polymer in water with petroleum ether, then saturating the aqueous monomer solution with sodium chloride, and extracting the monomer with chloroform. The combined chloroform extracts were dried over anhydrous magnesium sulfate and the solution distilled in vacuo (~0.1 mm on Hg) using cuprous chloride as inhibitor. The monomer fraction distilled over at 70°-82° C.

A copolymer of 52% butyl methacrylate, 40% HEMA, and 8% acrylic acid was prepared in the usual way, as described in Examples 1-13, employing 25% concentration of the monomers in a mixture of ethyl alcohol and dioxane.

Optically clear blends of the copolymer in varying proportions with poly(vinyl pyrrolidone) (PVP, Grade K-90, mol. wt. 360,000) were prepared as described in Examples 1-13 by dissolving the copolymer and PVP in dimethylformamide and subsequently evaporating the solvent at 100° C. in vacuo. Approximately 8-12 mil thick sheets of the blends were compression molded, after which they were equilibrated in deionized water at room temperature for 72 hours. It was found that blends containing 70, 80 and 90% by weight, respectively, of PVP formed hydrogels containing 75.8%, 82.3% and 88.9% by weight of water, respectively.

EXAMPLES 20-26

A copolymer of 62% butyl methacrylate, 8% acrylic acid, and 30% methacrylamide was prepared by the same general method as described in Examples 1-13, and optically clear blends of the resultant copolymer with varying amounts of the same poly(vinyl pyrrolidone), Grade K-90, were prepared as described in Examples 16-19.

It was found that a linear relationship existed between the proportion (10 to 40%) of the copolymer in the blend and equilibrium water content of the hydrogels as shown in column A of Table III below. In order to take into account the change in the properties of the PVP in the blend due to incorporation of the copolymer, hydration of the PVP fraction alone was calculated assuming that swelling of the copolymer in water is negligible, as shown in the last column of Table III. Once again it was found that equilibrium water uptake of the PVP fraction was inversely proportional to the amount of copolymer in the blend.

TABLE III

| BLEND COMPOSITION | | HYDROGEL COMPOSITIONS | | | |
| --- | --- | --- | --- | --- | --- |
| Co-polymer Wt. % | PVP Wt. % | A* | B* | C* | $\frac{100 \times W_{H_2O}}{W_{PVP} + W_{H_2O}} = \frac{A \times 100}{A + C}$ % H$_2$O in Hydrated PVP |
| 10 | 90 | 83.5 | 16.5 | 14.85 | 84.90 |
| 15 | 85 | 79.1 | 20.9 | 17.765 | 81.67 |
| 20 | 80 | 77.7 | 22.3 | 17.84 | 81.33 |
| 25 | 75 | 69.6 | 30.4 | 22.80 | 75.32 |
| 30 | 70 | 64.3 | 35.7 | 24.99 | 72.01 |
| 35 | 65 | 61.7 | 38.3 | 24.895 | 71.25 |

TABLE III-continued

| BLEND COMPOSITION | | HYDROGEN COMPOSITIONS | | | |
|---|---|---|---|---|---|
| Co-polymer Wt. % | PVP Wt. % | A* | B* | C* | $\dfrac{100 \times W_{H_2O}}{W_{PVP} + W_{H_2O}} = \dfrac{A \times 100}{A + C}$ % H$_2$O in Hydrated PVP |
| 40 | 60 | 55.3 | 44.7 | 26.82 | 67.34 |

$A^* = \dfrac{100 \times W_{H_2O}}{W_{Blend} + W_{H_2O}}$ $B^* = \dfrac{100 \times W_{Blend}}{W_{Blend} \ W_{H_2O}}$ $C^* = \dfrac{100 \times W_{PVP}}{W_{Blend} + W_{H_2O}}$

EXAMPLES 27-34

A series of water-soluble 1-vinyl-2-pyrrolidone copolymers containing varying proportions of vinyl acetate, N,N-dimethylacrylamide, and mixtures of both of the latter two was prepared by dissolving the desired proportions of monomers in equal volumes of methanol and by employing as initiator approximately 0.15% by weight (based on monomers) of a free radical generator such as 2,2'-azobisisobutyronitrile. Polymerization was carried out under solvent reflux conditions to a degree of conversion of about 90–95%, and the copolymer was obtained as a residual brittle transparent and colorless solid after evaporation of solvent and residual monomers by heating the reaction mix at 100° C. under vacuum.

A water-insoluble copolymer of a mixture of 62 parts by weight of n-butyl methacrylate, 30 parts of methacrylamide, and 8 parts of acrylic acid was prepared by the procedure described in Examples 1–13.

Blends of the water-soluble and water-insoluble copolymers were prepared as described in Examples 16–19.

The compositions of the vinyl pyrrolidone copolymers, the amounts of the copolymers in blends with the water-insoluble copolymer, and the equilibrium water content of each hydrogel blend in deionized water at room temperature after 72 hours are set forth in the following table. In each case the blends were optically transparent solids, forming optically transparent hydrogels when equilibrated in water.

TABLE IV

| Example No. | Water-Soluble Copolymer Mole Ratio | | | Blend Parts by Weight of Water-soluble Copolymer per 100 Parts of Blend | Equilibrium Water Content Weight % |
|---|---|---|---|---|---|
| | DMA | VP | VA | | |
| 27 | — | 50 | 50 | 90 | 70 |
| 28 | — | 50 | 50 | 70 | 59 |
| 29 | 90 | 10 | — | 90 | 77 |
| 30 | 90 | 10 | — | 70 | 65 |
| 31 | 70 | 30 | — | 90 | 79 |
| 32 | 70 | 30 | — | 70 | 67 |
| 33 | 50 | 25 | 25 | 90 | 76 |
| 34 | 50 | 25 | 25 | 70 | 65 |

DMA - N,N-Dimethylacrylamide
VP - N-Vinyl Pyrrolidone
VA - vinyl Acetate

The blends of the present invention possess the properties of thermoplasticity, fusibility, and solubility in organic solvents as well as hydratability. But while they retain the thermoplasticity, fusibility, and solubility in organic solvents of the vinyl lactam polymer or copolymer portion of the blend, they exhibit varying hydration characteristics of that portion depending upon the amount of copolymer present.

What is claimed is:

1. A composition capable of absorbing more than 45% of its weight of water without dissolution at room temperature to form an optically clear hydrogel consisting essentially of an optically clear blend of (1) 40 to 98% by weight, based on the total weight of the blend, of a water-soluble polymer of N-vinyl-2-pyrrolidone, having a molecular weight from 10,000 to 1,000,000 and (2) 2 to 60% by weight of a water-insoluble copolymer consisting essentially of 50 to 90% by weight, based on the total weight of the copolymer, of a hydrophobic water-insoluble ethylenically unsaturated monomer, 2 to 12% by weight of an ethylenically unsaturated monomer containing an acid group, and from 15 to 45% by weight of a hydrophilic ethylenically unsaturated monomer free from acidic groups.

2. A composition capable of absorbing more than 45% of its weight of water without dissolution at room temperature to form an optically clear hydrogel consisting essentially of an optically clear blend of (1) 40 to 98% by weight, based on the total weight of the blend, of a water-soluble polymer of N-vinyl-2-pyrrolidone, having a molecular weight from 10,000 to 1,000,000 and (2) 2 to 60% by weight of a water-insoluble copolymer consisting essentially of 88 to 90% by weight, based on the total weight of the copolymer, of methyl methacrylate and 10 to 12% by weight of 2-acrylamido-2-methyl propanesulfonic acid.

3. A composition as claimed in claim 1 in which said water-insoluble copolymer consists essentially of 55 to 70% by weight, based on the total weight of the polymer, of a monomer selected from the group consisting of methyl methacrylate, styrene, and 2-ethylhexyl acrylate, 2 to 12% by weight of acrylic acid, and methacrylamide in an amount from 25 to 43% by weight.

4. A composition as claimed in claim 1 in which said water-insoluble copolymer consists essentially of 55 to 80% by weight of n-butyl methacrylate, based on the total weight of the copolymer, 2 to 12% by weight of acrylic acid, and methacrylamide in an amount from 15 to 35% by weight.

5. A composition as claimed in claim 1 in which said water-insoluble copolymer consists essentially of 50 to 78% by weight, based on the total weight of the copolymer, of n-butyl methacrylate, 2 to 12% by weight of acrylic acid, and from 20 to 35% by weight of p-styrene sulfonamide.

6. A composition as claimed in claim 1 in which said water-insoluble copolymer consists essentially of 55 to 70% by weight, based on the total weight of the copolymer, of n-butyl methacrylate, 2 to 12% by weight of acrylic acid, and from 25 to 43% by weight of hydroxyethyl methacrylate.

7. A composition capable of absorbing more than 45% of its weight of water without dissolution at room temperature to form an optically clear hydrogel consisting essentially of an optically clear blend of (1) 40 to 98% by weight, based on the total weight of the blend, of a water-soluble polymer of a vinyl lactam having the structure

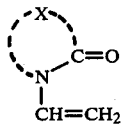

in which X represents an alkylene bridge having three to five carbon atoms, or a water-soluble copolymer thereof with 1 to 90 mole percent of copolymerizable monomer containing a polymerizable ethylenic unsaturation, said polymer or copolymer having a molecular weight from 10,000 to 1,000,000 and (2) 2 to 60% by weight of a water-insoluble copolymer consisting essentially of 50 to 90% by weight, based on the total weight of the copolymer, of a hydrophobic water-insoluble ethylenically unsaturated monomer, 2 to 12% by weight of an ethylenically unsaturated monomer containing an acid group, and from 15 to 45% by weight of a hydrophilic ethylenically unsaturated monomer free from acidic groups.

8. A composition capable of absorbing more than 45% of its weight of water without dissolution at room temperature to form an optically clear hydrogel consisting essentially of an optically clear blend of (1) 40 to 98% by weight, based on the total weight of the blend, of a water-soluble polymer of a vinyl lactam having the structure

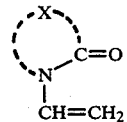

in which X represents an alkylene bridge having three to five carbon atoms, or a water-soluble copolymer thereof with 1 to 90 mole percent of copolymerizable monomer containing a polymerizable ethylenic unsaturation, said polymer or copolymer having a molecular weight from 10,000 to 1,000,000 and (2) 2 to 60% by weight of a water-soluble copolymer consisting essentially of 88 to 90% by weight, based on the total weight of the copolymer, of methyl methacrylate and 10 to 12% by weight of 2-acrylamido-2-methyl propanesulfonic acid.

9. A composition as claimed in claims 7 or 8 in which said vinyl lactam is N-vinyl-2-pyrrolidone.

10. A soft contact lens made of the composition claimed in claim 7.

11. A burn and wound dressing made of the composition claimed in claim 7.

* * * * *

UNITED STATES PATENT AND TRADEMARK OFFICE
CERTIFICATE OF CORRECTION

PATENT NO. : 4,300,820

DATED : November 17, 1981

INVENTOR(S) : Kishore R. Shah

It is certified that error appears in the above—identified patent and that said Letters Patent are hereby corrected as shown below:

Column 1, line 7, "1979" should be --1978--;

Column 12, line 21, "water-soluble" should be --water-insoluble--.

Signed and Sealed this

Second Day of February 1982

[SEAL]

Attest:

Attesting Officer

GERALD J. MOSSINGHOFF

Commissioner of Patents and Trademarks